United States Patent
Weil et al.

(10) Patent No.: US 8,709,380 B1
(45) Date of Patent: Apr. 29, 2014

(54) TARGETING AGENTS FOR ENHANCING RADIATION THERAPY

(75) Inventors: Michael D. Weil, Fort Collins, CO (US); Kevin N. Morris, Denver, CO (US); Rainer M. Malzbender, Niwot, CO (US)

(73) Assignee: Sirius Medicine, LLC, Fort Collins, CO (US)

( * ) Notice: Subject to any disclaimer, the term of this patent is extended or adjusted under 35 U.S.C. 154(b) by 1554 days.

(21) Appl. No.: 11/671,222

(22) Filed: Feb. 5, 2007

Related U.S. Application Data

(60) Provisional application No. 60/765,971, filed on Feb. 7, 2006.

(51) Int. Cl.

| | | |
|---|---|---|
| *A61K 51/00* | (2006.01) | |
| *A61M 36/14* | (2006.01) | |
| *A61K 49/04* | (2006.01) | |
| *A61K 41/00* | (2006.01) | |
| *A61K 9/00* | (2006.01) | |

(52) U.S. Cl.
CPC ............. *A61K 49/04* (2013.01); *A61K 41/0038* (2013.01); *A61K 9/0019* (2013.01)
USPC ........................................................ 424/1.61

(58) Field of Classification Search
None
See application file for complete search history.

(56) References Cited

U.S. PATENT DOCUMENTS

| | | | | |
|---|---|---|---|---|
| 4,385,634 | A * | 5/1983 | Bowen ........................... | 600/407 |
| 4,744,922 | A * | 5/1988 | Blakely et al. ................. | 252/478 |
| 5,071,775 | A * | 12/1991 | Snapka et al. ................. | 436/545 |
| 5,902,825 | A * | 5/1999 | Jia .................................. | 514/492 |
| 6,149,889 | A * | 11/2000 | Chin et al. ...................... | 424/1.61 |
| 6,592,843 | B2 * | 7/2003 | Larsen et al. .................. | 424/1.21 |
| 6,635,234 | B1 * | 10/2003 | Larsen et al. .................. | 424/1.11 |
| 6,767,531 | B2 * | 7/2004 | Fritzberg et al. .............. | 424/1.65 |
| 7,056,275 | B2 * | 6/2006 | Larsen et al. ...................... | 600/3 |
| 2001/0019709 | A1 * | 9/2001 | Krause et al. ................. | 424/1.65 |
| 2006/0210479 | A1 * | 9/2006 | Young et al. ................. | 424/9.363 |
| 2008/0241074 | A1 * | 10/2008 | Bornhop et al. ........... | 424/9.363 |

OTHER PUBLICATIONS

Friedman (Curr. Pharm. Des. 2002, 8, 1765-1780).*

* cited by examiner

*Primary Examiner* — Michael G Hartley
*Assistant Examiner* — Melissa Perreira

(57) ABSTRACT

Targeting agents are provided that have an affinity for aberrant cells and tissues. These agents are comprised of chelates, ligands, and/or particles combined with high atomic weight elements so that treatment with ionizing electromagnetic radiation (X-rays, or Gamma rays) results in a higher dose to aberrant cells and tissues than other cells and tissues of a host. The invention further provide methods to enhance the tumor to normal tissue damage ratio by concentrating agents with high atomic number elements to the site of the tumor prior to administering radiotherapy. The result is greater therapeutic efficacy with fewer side effects. These compounds also permit diagnostic uses in combination with the therapeutic use.

8 Claims, 4 Drawing Sheets

TARGETING AGENTS FOR ENHANCING RADIATION THERAPY

RELATED U.S. APPLICATION DATA

This application claims priority of provisional application No. 60/765,971 filed Feb. 5, 2006 and entitled, Targeting Agents for Enhancing Radiation Therapy.

REFERENCES CITED

U.S. Patent Documents

U.S. Pat. No. 4,882,142 November 1989 Simon et al.
U.S. Pat. No. 5,928,627 July 1999 Kiefer et al.
U.S. Pat. No. 6,125,295 September 2000 Cash and Weil
U.S. Pat. No. 6,366,801 April 2002 Cash and Weil
20020165179 November 2002 Baker
20030118508 June 2003 Simon et al.
20030215392 November 2003 Lanza et al.
20030228256 December 2003 Inverardi et al.
U.S. Pat. No. 6,955,639 October 2005 Hainfeld and Slatkin
Ser. No. 60/765,971 February 2006 Weil et al.

OTHER PUBLICATIONS

Morris et al., "Radiochromic film dosimetry of contrast-enhanced radiotherapy (CERT)," Phys. Med. Biol. 51:5915, 2006, Inst. Phys. Pub.

Weil et al., "Phase I Study of Contrast-Enhanced Radiotherapy with GMCSF for Advanced Cancers," Submitted, 2007.

FIELD OF THE INVENTION

This invention relates to the fields of radiation therapy where a patient is given radiation to destroy tissues and cellular growths that are detrimental to the body. More specifically, this invention relates to the use of novel contrast agents, or radiosensitizers to enhance treatment of a patient with radiation.

BACKGROUND OF THE INVENTION

Radiation is extensively used for the treatment of cancer and other diseased cells and tissues. Radiation therapy consists of exposing part or all of the body to a field of ionizing electromagnetic radiation. Often performed at 1 MeV or higher, the goal is to damage diseased cells. Although healthy cells frequently receive high radiation doses during such treatment, the healthy cells, ideally, are better able to repair the damage and remain viable while the diseased cells die.

The effectiveness of conventional radiation therapy is limited by insufficient radiation dosing due to the need to reduce radiation to normal cells and tissues. In many cases, the radiation dose to a tumor is the same as the dose to other tissues, especially surrounding tissues. This leads to significant toxicity in healthy cells. In order to increase the ratio of the dose to the intended target versus normal tissue (non target), radiation is often introduced to the tumor from different angles to reduce injury to skin and overlying tissue. However the x-rays also spread beyond the tumor and overshoot the target. The result is significant toxicity to an organism due to dosing of normal tissues.

Contrast agents are used to enhance the effect of x-rays for treatment of aberrant tissue. (U.S. Pat. Nos. 6,125,295 and 6,366,801). For example, a contrast agent is normally delivered to a tumor mass prior to delivering the radiation dose. These contrast agents have, as a component, an element with a high atomic number (Z), such as iodine or gold. The interaction between the ionizing radiation and the greater cross-section of the high Z material creates additional ionizations that result in greater cell toxicity at the site of the tumor.

Contrast agents also improve the accuracy of assessing a disease state. To be useful, the contrast material must be delivered to the area where a suspected abnormality may be present for radiation exposure to result in high enough contrast for a successful diagnosis However, conventional contrast agents have the disadvantage that they lack affinity for the cells and tissues to be treated so that the residence time of the agent in the targeted tissue is short. The poor uptake of the conventional contrast agent by a tumor means that the agent needs to be applied directly into the tumor. Furthermore, the contrast agents migrate out of the tumor quickly and delivery of the radiation is required very soon after administering the contrast agent, often within one hour. If delivered by intravenous administration, common contrast agents often require relatively large volumes of contrast agent solution to be administered within a short period of time e.g., 100 ml within one minute. This creates a risk of rapid allergic reaction and can cause discomfort to the patient.

To achieve more specific cellular and tissue targeting with these agents, they are typically modified using a biological carrier such as a protein, or a monoclonal antibody, or fragments thereof. Thus a monoclonal antibody combined with a payload of iodine or other heavy element can be used to more selectively deliver high Z atoms to a tumor. These agents have been shown to be useful for the treatment (when the elements themselves are radioactive isotopes) and diagnosis of cancers. However, the biodistribution of these systems is unfavorable to enhance radiation therapy when the elements are not radioactive. In addition, the retention time of the dose in blood when radioactive elements are used is long, and usually only a small portion of the dose is observed at the site of the tumor. Unfortunately, the density of antigen sites that the tumor can present is low and so the potential amount of high Z material that can be delivered is relatively low. Better agents are needed to enhance the effect of radiation at tumor sites.

SUMMARY OF THE INVENTION

It is an object of this invention to provide a method for increasing, the effectiveness of radiation therapy by delivering an effective amount of a targeting agent to diseased cells or tissue, followed by administration of radiation therapy, external or seed-based, to the diseased cells or tissue. The targeted cells or tissue can be tumors, such as cancer, or pathogen-infected cells, or even unwanted tissue resulting from autoimmune disease. These targeting agents can also be used to enhance contrast for diagnostic use.

The targeting agents of this invention include iodinated X-ray contrast agents and gadolinium (Gd)-based MR (magnetic resonance) contrast agents that are modified to enhance damage to unwanted cells and tissues of a body so that less radiation can be used during radiation treatments. Enhancement through these novel agents is provided by their affinity and selectivity for the unwanted target cells and tissues and the ability to bind a high concentration of heavy metal elements.

It is another object of this invention to provide targeting agents that are bone-targeting chelates, a soft tissue targeting chelates, a high payload targeting systems, or combinations thereof. The targeting agents can be a chelate complexed with at least one element having an atomic number (Z) greater than 38. More specifically, the chelate is selected from the following group: ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), tris(2-aminoethyl) aminehexamethylenephosphonic acid (TTHMP), 1-carboxyethylenediaminetetramethylenephosphonic acid (CEDTMP) and bis(aminoethylpiperazine)tetramethylenephosphonic acid (AEPTMP). Ethylenediaminetetraacetic acid (EDTA), 1,4,7,10-tetraazacyclododecane-N,N',N'',N'''-tetramethylenephosphonic acid (DOTMP), hydroxyethyldiphosphonic acid (HEDP), methylenediphosphonic acid (MDP), diethylenetriaminepentaacetic acid (DTPA), hydroxethylethylenediaminetriacetic acid (HEDTA), and nitrilotriacetic acid (NTA).

The methods provided herein use targeting agents having at least one element having an atomic number (Z) greater than 38. Targeting agents, therefore, can contain Y, In, Re, Gd, Sn, La, Ac, Ra, Pm, Sc, Sr, Ra and Ag, W, Ir, Pt, Au, and Bi or a combination thereof. More specifically, the element is a transition, or other metal, preferably a lanthanide metal.

In preferred embodiments, the targeting agent contains EDTMP or DOTMP, especially Gd-EDTMP or Gd-DOTMP. The targeting agent can also be selected from the group consisting of Sn-DTPA or Re-HEDP.

It is a further object of this invention to provide methods and composition for the treatment and diagnostics of primary or metastatic bone cancer, or other primary or metastatic cancers, osteomyelitis, full or partial ablation of bone marrow, and brain cancers. The methods can be used either before or after surgery to remove tumorous growths or diseased tissues.

Further, the targeting agent can be a soft tissue cancer-targeting agent comprising a tetraaza macrocyclic amine chelator with half ester phosphonic acid functionality capable of targeting soft tissue cancers. In preferred embodiments, the heavy element of the targeting agent is chosen from the transition, or other metal elements, or the lanthanide series, more particularly Gd, Er or Lu. The composition of the targeting agent can include PCTMB or QCTME.

It is another object of this invention to provide methods of treatment and/or diagnostics wherein the targeting agent is a high payload system consisting of a polymer or a particle capable of carrying a high payload comprising at least one high atomic weight element and a targeting moiety. The targeting agents of this method have heavy atomic weight elements chosen from the transition, or other metal elements, or particularly the lanthanide series. In preferred embodiments, the polymer will be a fluorocarbon, a polyamine, a dendrimer, a viral particle, a liposome, or a particle is selected from gold or silicone or albumin.

It is another object of this invention to provide a method of radiation dosimetry for treatment using the mass energy-absorption coefficients (MEAC) for the entire beam spectrum and according to the effects of the tissue type and depth of tissue, as well as the contrast type and depth of contrast, to calculate the dose enhancement factor (DEF). The methods can be used to compare the mass absorption coefficients (MAC) and the mass energy-absorption coefficients (MEAC) of a high Z element compared to iodine, or other contrast agent, to optimize the selection of high Z element to use in a chelate or contrast for treatment.

DETAILED DESCRIPTION OF THE INVENTION

Figure 1:
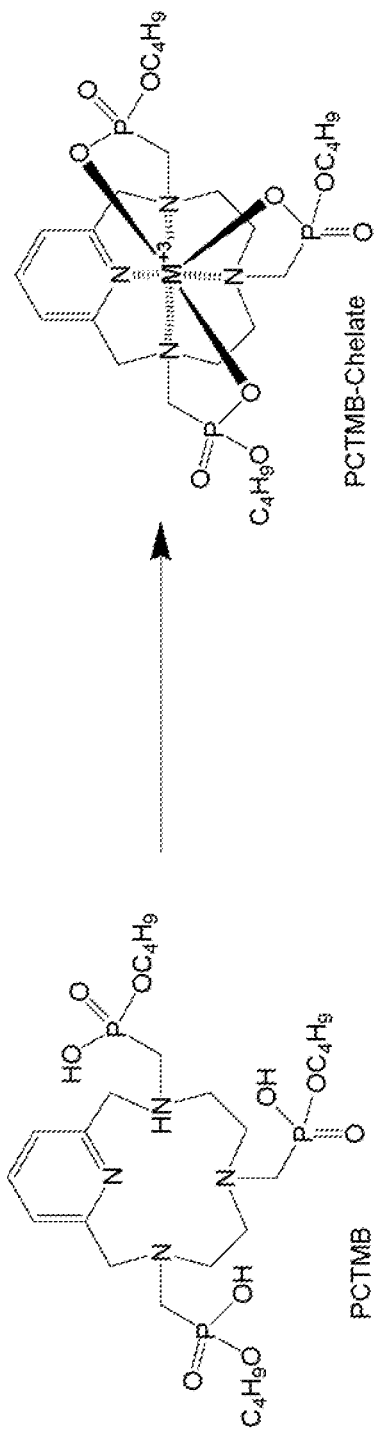
FIG. 1 illustrates examples of chelates constructed from polyazamacrocyclic compounds modified to combine high Z elements (M).

One of the most difficult problems in radiation treatment is how to deliver radiation to diseased cells and tissues without adversely affecting normal host cells and tissues. Radiation is regularly used to damage or kill diseased or unwanted cells or tissues, especially cancer cells. Until now however, it was difficult to reduce levels of radiation because of the difficulty of concentrating damaging photons in the desired target areas of the host. Agents that can be used to concentrate radiation also have the potential to better delineate target areas for diagnostics as well.

This invention provides targeting agents that have an affinity to the site of a tumor or other aberrant cells or tissues, and that carry and/or maintain an adequate amount of high atomic weight (Z) metal to such tissues. The targeting agents of this invention have an affinity for tumor or cancer cells, or the ability to concentrate in the vicinity of tumor, and/or can carry a high concentration of heavy elements to the site of the tumor. Further, these targeting agents can have the ability to penetrate cells.

The effect of these targeting agents is to achieve a high concentration of a heavy element at the target site and a low concentration elsewhere thereby protecting normal tissue from radiation. A further advantage is to maintain the heavy element at the target site so that it is not expelled quickly from the organism and it remains at the target site long enough to provide adequate time for radiation to be focused on and administered effectively to the target site.

These agents are especially important for treatment of numerous small tumors or cells that cannot be injected directly with contrast agents. Thus, whole body radiotherapy can be accomplished over a longer period of time in low doses while the heavy elements concentrated at the diseased sites enhance the absorption of radiation to these sites compared to normal cells and tissues. In this manner, contrast of such tumors or diseased cells is also enhanced so that diagnostic clinicians have a better understanding of the spread of a disease.

Further, these targeting agents can include radioactive "seeds" for implantation at the target site in the body. These seeds emit radiation in all directions, increasing the likelihood of damage to healthy tissue. Combined with targeting agents, however, that attenuate radiation quickly, there is less chance of the radiation traveling to normal tissues. The targeting agents of this invention keep the radiation concentrated in the area of the aberrant tissue. Overall, the methods of this invention increase the cross-section, or stopping power of the target, because more photons are deposited in the target cells or tissues. This results in increasing the cross-section of a tumor or other aberrant tissue to radiation relative to the cross-section of normal tissue; i.e., more dose is deposited at the target.

The agents of this invention are primarily heavy element ligand complexes or chelates. The types of chelates are divided up into three categories; bone targeting chelates, soft-tissue tumor targeting chelates, and high payload targeting systems.

By chelate, it is meant an organic molecule that can trap or encapsulate metal cations into a soluble but bound form.

Chelates are a class of coordination or complex compounds consisting of a central metal atom attached to a large molecule, called a ligand, in a cyclic or ring structure. These metal-chelate complexes can deliver selected mineral elements with maximum tolerability and safety. Metal chelates can introduce the right kind of metal ion into a tumor in precisely the right dose.

Ligands are any atom or molecule attached to a central atom, usually metallic element, in a coordination or complex compound. The atoms and molecules used as ligands are almost always those that are capable of functioning as the electron-pair donor in the electron-pair covalent bond formed with the metal atom.

As used herein, patient or host can refer to a mammal, including humans, primates, dogs, cats, horses, mice, rats, and the like.

Selectivity or affinity, as used herein, refers to the recognition of targeted cells or tissues, as opposed to non-targeted (normal) cells or tissues. Specificity, refers to the recognition of a unique component of a cell, such as an antigen or receptor by a binding molecule.

The aberrant cells or tissues meant to be treated by the novel compounds and methods of this invention are those that are diagnosed as pathological, such as cancer or a non-malignant tumor, or those infected by a pathogen, or those affected by autoimmune disease. In other words, the target cells of the invention include any cell in a mammalian host which is undesirable and needs to be eliminated, controlled, attached and/or destroyed functionally or otherwise. In particular target cells can be tumor cells, especially cancer cells, bacteria-infected cells, virus-infected cells, or autoimmune cells. Treatment or diagnosis by radiation can be accomplished by radiotherapy (exposing the entire organism to radiation) or radiosurgery (treating a particular target in the organism with a high dose of radiation).

Bone-targeting chelates of this invention consist of a chelating agent complexed with a high Z element. The methods of invention includes the step of administering to a recipient with a bone lesion, a bone seeking agent, which is not a radiopharmaceutical, i.e., neither the agent nor are the heavy elements are radioactive, (a bone seeking radiopharmaceutical is defined herein to mean a complex of a radionuclide and a ligand which targets bone or calcified tissue rather than soft tissue). The bone tumor could be primary, metastatic, or a soft tissue tumor that has calcified. After localization of the targeting agent to the lesion, the area of the lesion is then treated with radiation.

The radiation can be delivered by either an external radiation beam, e.g. an X-ray beam, or via brachytherapy (localized, radioactive seeds). This invention does not employ radiopharmaceuticals. Rather, a bone-seeking pharmaceutical of this invention is defined herein to mean a complex of a heavy element and a ligand which targets bone or calcified tissue rather than soft tissue. Preferably, the pharmaceutical comprises a heavy element, or a transition, or other metal, or lanthanide heavy element, complexed with an aminophosphonic acid. Preferred heavy elemental ions include atoms chosen from the lanthanide series, or other high Z material. For example, La, Ce, Pr, Nd, Sm, Eu, Gd, Tb, Dy, Ho, Er, Tm, Yb, Lu and Ag, W, Re, Os, Ir, Pt, Au or Bi are heavy atoms of this invention. Other heavy elemental ions can also be used, as long as they have high atomic numbers and affinity for a bone tumor when introduce into the body. Other non-limiting examples of elements of this invention include Y, In, Re, Sn, La, Ac, Ra, Pm, Sc, Sr, and Ra.

Preferred ligands include aminophosphonic acids and lower carboxylic acids. More preferably, the ligand is selected from the group consisting of: ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), tris(2-aminoethyl) aminehexamethylenephosphonic acid (TTHMP), 1-carboxyethylenediaminetetramethylenephosphonic acid (CEDTMP) and bis(aminoethylpiperazine)tetramethylenephosphonic acid (AEPTMP). Ethylenediaminetetraacetic acid (EDTA), 1,4,7,10-tetraazacyclododecane-N,N',N",N'''-tetramethylenephosphonic acid (DOTMP), hydroxyethyldiphosphonic acid (HEDP), methylenediphosphonic acid (MDP), diethylenetriaminepentaacetic acid (DTPA), hydroxethylethylenediaminetriacetic acid (HEDTA), and nitrilotriacetic acid (NTA).

Preferably, the bone-seeking pharmaceutical complex is chosen from the group consisting of a transition, or other metal elemental ion, or lanthanide, and either EDTMP or DOTMP. Specific examples include X-EDTMP, X-DOTMP, Ho-EDTMP, Ho-DOTMP, Gd-EDTMP, Gd-DOTMP, Dy-EDTMP, Dy-DOTMP, Lu-EDTMP, Lu-DOTMP (where "X" is a heavy element). Other bone-seeking agents such as Re-HEDP, and Sn-DTPA are included in this invention.

Generally the bone-seeking chelates described above are made in an aqueous solution. Administration is accomplished by intravenous (i.v.), interstitial, or intramuscular administration. In order to increase the amount of heavy atom concentration at the site of the tumor, the bone-targeting agents of this invention can be administered by a slow continuous infusion in the bloodstream keeping a high concentration in the bloodstream until the desired amount of contrast agent is in the tumor. Alternatively, a tourniquet can be used to isolate the site of the tumor prior to administering the dose to increase uptake in the tumor. The concentration of the agent required at the target can be determined by imaging with a CT scanner, or other imaging device.

Among the types of tumors that can be diagnosed and treated by this invention are primary bone tumors, metastatic bone tumors, and soft tissue tumors that have calcified. If a tumor has not metastasized, the bone-targeting agent can be administered and the radiation concentrated to the area of the tumor to reduce toxicity to normal cells and tissues; i.e., increasing the target to non-target ratio of absorbed radiation dose. Where numerous tumors are in need of treatment, or in the case of disseminated disease, it is possible to administer the bone-targeting agent, then give radiation to the whole body. This manner of radiation administration can treat micro metastatic sites, or small tumors, before they grow into large and less treatable tumors.

This invention further provides methods to reduce toxicity to patient when it is necessary to obliterate bone marrow in preparation for transplantation with donor bone marrow cells. Allogeneic bone marrow transplantation (BMT) has evolved from an experimental procedure reserved for patients with refractory leukemia into a rapidly expanding area of clinical investigation that offers potential cure for patients with aplastic anemia, acute and chronic leukemia, breast cancer, and selected types of lymphoma. Pediatric BMT has expanded because of its potential for curing children with genetic diseases such as sickle cell anemia, immunodeficiencies, thalassemia, and inborn errors of metabolism. The objective of BMT is to provide a healthy stem cell population that will differentiate into blood cells to replace deficient or pathologic cells of the host.

For individuals afflicted with disease in the bone marrow, it is necessary to obliterate the marrow prior to introduction of new marrow. Normally, bone marrow ablation is accomplished by administration of cytotoxic drugs, followed by a whole body dose of external beam radiation. The high radiation dose required to fully ablate the internal marrow results in a significant radiation dose to tissues and organs outside the marrow. In fact, the dose is uniform throughout the body, so the whole body receives the same dose. Because bone marrow is a relatively fast growing tissue, it is more sensitive to the effects of radiation. Thus, selective ablation of bone marrow depends on the higher sensitivity of the marrow to radiation compared to other parts of the body. However, levels of external beam radiation high enough to ablate the marrow lead to significant overall damage and toxicity to the patient.

A less toxic method to ablate bone marrow has been described (U.S. Pat. No. 4,882,142). However, the technique involves insertion of large amount of beta-emitting radioactive metal to the bone and, depending on the dose from bone to bone marrow, requires handling and delivering high doses of radioactive material. Ultimately, this method is limited because greater than 50% of complexes of this type are cleared via the liver or kidney, presenting considerable toxicity issues.

This invention provides a more effective and less toxic method for ablating bone. Instead of delivering radioactive material to the marrow, it involves administration of non-radioactive heavy element-based bone agents prior to delivering whole body external beam irradiation or radioactive seeds. The loading of the bone with heavy elements enhances the target to non-target ratios of radiation dose such that it is possible to deliver lower total radiation and thus decreasing the toxic side effects to the rest of the body. Yet another aim of this invention is to provide a safer method to obtain partial ablation of the bone marrow. One example of how partial bone marrow ablation is useful is described in U.S. patent application 20030228256 A1 where partial bone marrow damage is used to achieve macrochimerism and achieve transplant tolerance. Through the methods of this invention, macrochimerism is more easily accomplished because the radiation dose is easier to control from outside the body of a host than by seeding the body with radioactive materials.

In another aspect, this invention provides a safer, direct method to treat osteomyelitis. Osteomyelitis is a serious bone infection that can manifest itself as a concentrated mass of pus in the bone or throughout one or more bones. It is difficult to treat with antibiotics because of the deep-seated nature of the infection in the hone. When long-term antibiotic treatment fails, chronic infection can result, leading to bone destruction, amputation, and life-threatening seeding of the infective microorganisms to cardiac valves, lungs, and the brain.

Radioactive pharmaceuticals have been proposed to treat osteomyelitis (U.S. Patent Publication No. 20030118508 A1) by inserting a radiopharmaceutical to the site of infection. The compounds provided herein can be used for a safer, more effective treatment of osteomyelitis by delivering a non-radioactive bone targeting agent to a site of an osteomyelitic lesion, followed by directed exposure of only the infected area to radiation.

This invention also provides methods and compositions for targeting soft tissue cancers. In the past, biological targeting moieties have been tried to increase injury to these cancers. The procedure uses a targeting moiety such as a protein, or a monoclonal antibody, or fragments thereof. Even though this technology can be used to deliver high Z materials to tumor cells, the amount that can be delivered to the tumor cell is relatively low and not adequate to cause a significant enhancement of dose when delivering radiation. Further, biological targeting moieties can be complex to produce, are fragile, and can elicit an allergic response from the body. Chelates, as non-proteinaceous compounds are less likely to elicit immune responses. There is a need for new contrast agents for the purpose of enhancing the radiation dose absorbed by the target. The ligands of this invention provide simple low molecular weight contrast agents that can deliver high Z elements directly to soft tissue cancers without serious side effects.

A series of fluorescent, phosphonic acid half esters has been described for diagnosing certain types of cancers (U.S. Pat. No. 5,928,627A). Fluorescent agents alone, however, are not useful for radiation therapy. Provided herein are chelates constructed from polyazamacrocyclic compounds (see for example, U.S. Pat. No. 5,928,627A), further modified to combine high Z elements for delivery to a tumor in order to enhance the effect of radiation therapy. The half ester macrocyclic chelates described below are defined as soft tissue, tumor-targeting chelates. For example, PCTMB is a macrocyclic amine chelating agent with the structure below and can be modified by adding a high Z material as shown in FIG. 1, where "M" is a high Z material.

These agents can be administered by any variety of standard methods. For example, direct injection into the tumor mass gives a high concentration of the high Z materials in the tumor. The neutral ionic charge and enhanced lipophilicity of these molecules can be used as a tool to modulate tumor residency time and facilitate optimal delivery of the therapeutic radiation dose with reduced damage to adjacent normal tissue. Typically, these chelate structures display high selectivity and specificity for abnormal cells and are known to permeate cell membranes and localize in the cytoplasm. This novel feature makes it possible to produce enhanced cell damage when combined with radiation therapy by creating an intracellular cascade of secondary radiation. Site-specific delivery of these intracellular agents can be accomplished through systemic, intralesional or topical application.

Soft tissue tumor-targeting chelates add considerable benefit in precise control of targeting agent diffusion since it is possible to moderate charge, polarity and receptor function and thereby tailor the residence time of the targeting chelates in the tumor. Quantification and dosimetry of the delivered dose of radiation are parameters influenced by the residence time of the targeting agent in the tumor and are dependent upon the kinetics of diffusion out of the target site. The amounts of targeting agent employed will be essentially the same as those amounts usually employed with contrast agents or with analogous agents for the given treatment modality as conventionally performed.

Other benefits of the invention include both extracellular and intracellular distribution of the agents (conventional contrast goes no further than the extracellular space). Use of targeting chelates in this manner can enhance the effect of external beam radiation or brachytherapy after direct injection into a tumor, an IV injection and topical applications. These kinds of advantageous chemical attributes are not possible with known iodinated x-ray contrast agents or gadolinium-based MR contrast agents.

Figure 2:
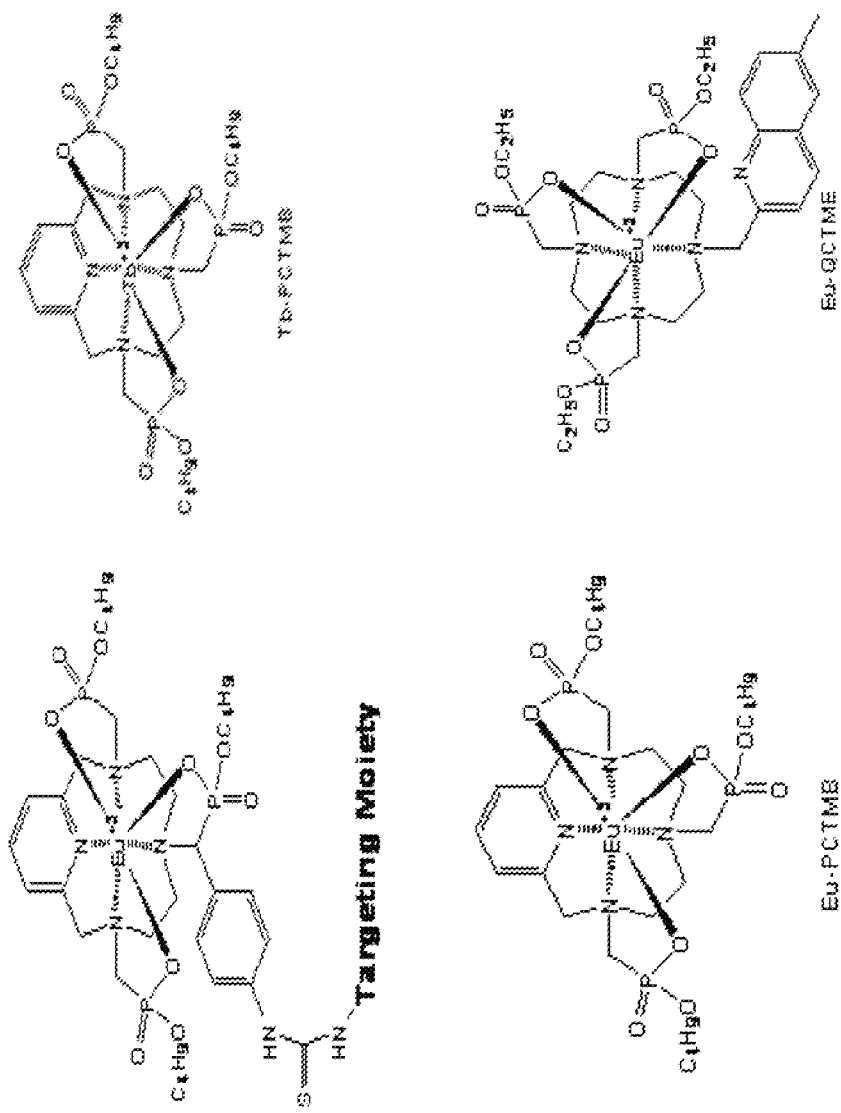
FIG. 2 portrays representative examples of useful targeting chelates for enhancement with therapeutic radiation.

Some representative examples of useful targeting chelates that will have valuable attributes for the enhancement with therapeutic radiation are illustrated in FIG. 2.

This invention also encompasses other types of targeting agents that can deliver a high payload (concentration of high atomic weight elements) to the site of the tumor or other target area. For example, polymers with a multiple reactive groups can be derivatized with a large number of targeting moieties plus a large number of metal chelates. More specifically, polyethylene imines have multiple amino hydrogens that can be derivatized as described above. Polymers of polyepichlorohydrin can be derivatized with amine functionality through reaction with ammonia or other amines thereby creating a polymer with multiple functional groups to which payloads can be attached. Dendrimers can also be derivatized with targeting moieties and a high payload of high Z materials as described in U.S. Patent Publication 20020165179 A1. A multiplicity of chelating agents has been delivered to sites of tumors using fluorocarbon emulsions as described in U.S. Patent Publication 20030215392 A1. In addition, liposomes, gold particles (see U.S. Pat. Nos. 6,125,295; 6,366,801 and 6,955,639), viral particles, and silicon particles are examples of carriers for high payloads of both targeting moieties and either imaging or therapeutic agents. In these technologies, targeting moieties plus radioactive atoms are bonded to the macromolecule and the formulation administered into cancer patients. Even though diagnostic applications for these systems are viable, therapeutic uses have been limited by the high accumulation of these radioactive agents in the liver and other parts of the reticuloendothelial system. The high doses of radioactive targeting moieties to these organs virtually prevent the use of the technology for treatment purposes. The non-radioactive high payload systems of this invention provide novel compounds and methods to enhance the effect of radiation therapy in a manner that has not been taught elsewhere. Most effectively, the affinity of the formulations for cancer cells allows whole body radiation therapy at lower doses to destroy undetectable metastatic cells at sites other than the original tumor.

Thus methods of this invention include the use of high payload systems with the ability to target cancer and other aberrant tissues. These high Z materials can be loaded on any type of particle by a variety of chelating agents. In particular, bifunctional chelating agents can be used to attach the heavy elements to the carrier molecules. These are chelating agents that have the ability to tightly complex heavy atoms and a functional group to the carrier molecule. The payload systems and bifunctional chelating agent combinations useful for this purpose are numerous. This invention is not limited to the carrier system or the method by which it is derivatized. The object is to administer a targeted, high payload system comprising a large number of targeting molecules to the patient so there is adequate uptake by the target area of the body. Dosage and uptake times can be standardized depending on the payload system, the means of administration, the location and type of diseased tissue, and other parameters such as the weight of the patient. Following uptake, a patient is given a dose of localized, therapeutic radiation.

The methods of this invention further provide a procedure to reduce radiation damage to brain tissues when radiation therapy is used to treat brain tumors or other diseased brain tissue. Targeting agents that increase absorption of radiation at the site of the tumor or diseased tissue compared to healthy brain tissue can be extremely beneficial since any extraneous radiation damage to normal brain tissue can have extremely serious effects.

The non-radioactive form of IOTREX™, sodium 3-(125I) iodo-4-hydroxybenzenesulfonate (the iodinated compound used with GliaSite™ Radiation Therapy System (Proxima Therapeutics, Inc., Alpharetta, Ga., 30005 U.S.A.) in the treatment of brain cancer can be utilized in these methods. IOTREX™ in radioactive form is used as the radiation source for the brachytherapy of resected brain tumor cavity margins. The treatment technique involves implanting an inflatable balloon catheter (GliaSite™ Radiation Therapy System) into the tumor cavity at the time of resection. Brachytherapy is initiated by filling the balloon with IOTREX™ solution. After completion of the treatment, the solution is removed from the balloon via an access port.

The use of a liquid radioactive source poses problems for clinicians and patients. Many clinical medical physicists are unfamiliar with handling of liquid radioactive sources and there are radiation safety concerns not just for them but also for the patients receiving the treatment.

It is likely that targeting chelates do not cross the blood-brain barrier. However, direct application of a targeting agent of this invention, including the possibility of a high atomic weight metal complexed with non-radioactive IOTREX™ can prove a safer and more effective treatment of brain tumors, especially following surgery. Treatment of brain cancers (primary and metastatic) is a potential application for CERT (Contrast-Enhanced Radiotherapy) as minimizing damage to healthy brain tissue would be very beneficial. Although, the targeting ability of the chelates might not be as direct as in lesions in the rest of the body, it could help substantially to minimize damage to healthy brain tissue. This has been demonstrated by treating a patient with brain tumors during a Phase I study in 1999. Alternatively, the properties of the targeting chelates can be altered to enable the molecule to cross the brain-blood barrier and maintain its ability to target cancer cells.

Further, targeting agents of this invention can be used with radioactive seeds in the treatment of brain lesions. Toxicity to surrounding tissues is reduced because the concentrations of high atomic weight elements maintain most of the ionizing radiation in the target area.

The radiation dosimetry can be optimized by selection of a high Z atom to form the chelate. The dose enhancement factor (DEF) of the high Z element (Z) is determined by the equation:

$$DEF = \frac{(\mu_{en}/\rho)_Z * f_Z + (\mu_{en}/\rho)_{target} * (1 - f_Z)}{(\mu_{en}/\rho)_{tissue}}$$

Where $(\mu_{en}/\rho)_Z$, $(\mu_{en}/\rho)_{target}$ and $(\mu_{en}/\rho)_{tissue}$ are the mass energy-absorption coefficients (MEAC) of the high Z element of choice, the target and tissue, respectively at the employed beam energy; and $f_Z$ is the fraction by weight of the high Z element. Since the X-rays from a medical source are a spectrum of energies, the MEAC values are calculated over that spectrum to accurately determine the DEF (Morris et al., "Radiochromic film dosimetry of contrast-enhanced radiotherapy (CERT)," Phys. Med. Biol. 51:5915, 2006, Inst. Phys. Pub.).

The penetration of the radiation through tissue will decrease the flux and also change the spectrum by hardening the beam; i.e., the average beam energy increases as lower energy photons are attenuated and higher energy photons relatively predominate. As a result of the radiation's path, the beam spectrum changes with tissue type and depth, as well as high Z atom type, concentration and volume in the target. In clinical practice, these variables are accounted for and the DEF is calculated with planning software (Weil et al., "Phase I Study of Contrast-Enhanced Radiotherapy with GMCSF for Advanced Cancers," Submitted, 2007).

The attenuation of the radiation is determined by the mass attenuation coefficient (MAC)—where $(\mu/\rho)_Z$ is the MAC for a given high Z element. By comparing a high atomic weight element's MAC and MEAC to that of iodine in specific clinical scenarios, the selection of a high Z element in a chelate can be customized to improve the radiation dosimetry. By using this calculation, the enhancement of the radiation dose in the target is further optimized compared to what could be accomplished with conventional CT contrast agents.

Figure 3:
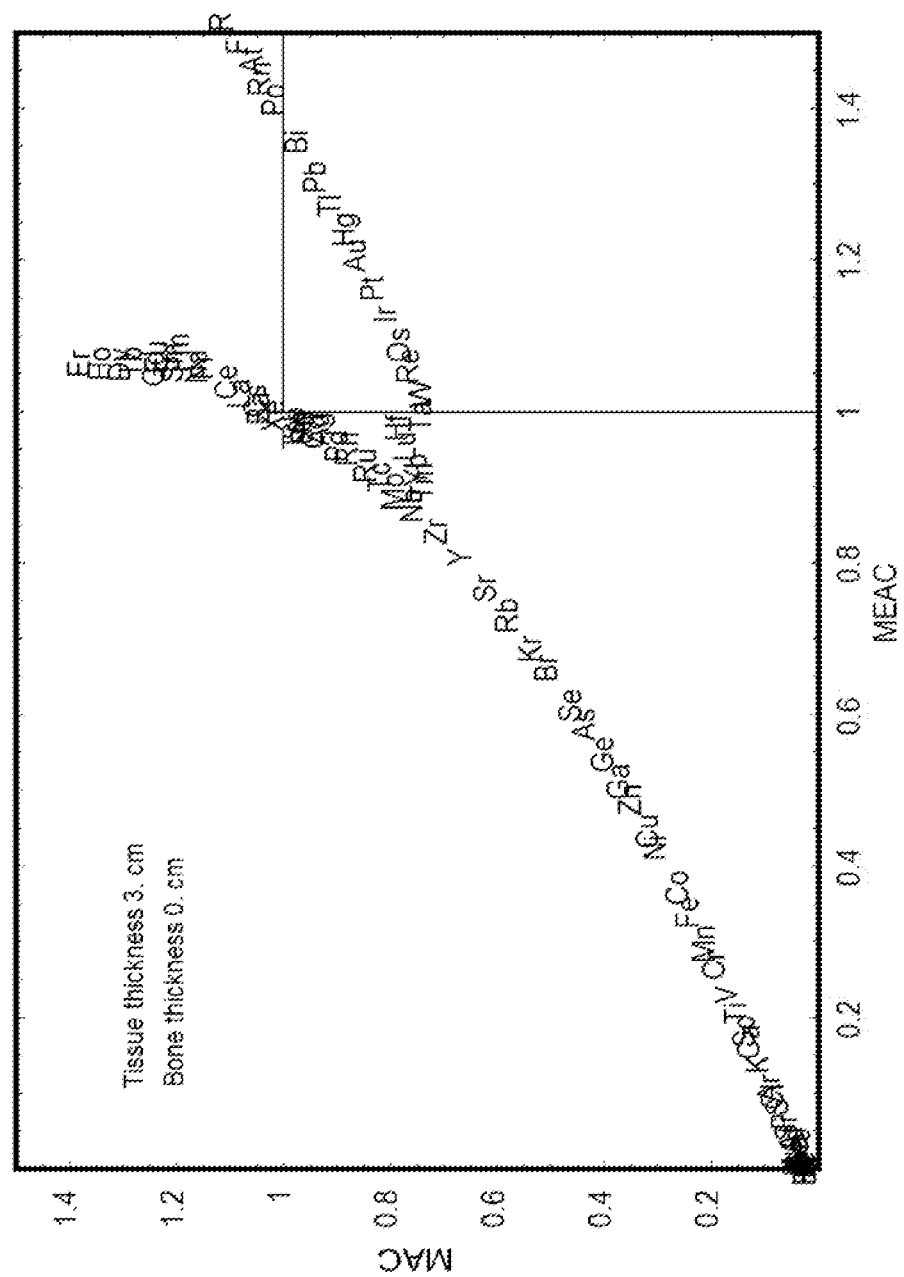
FIG. 3 depicts a 3 cm path of a 140 kVp X-ray beam through tissue without bone.
Figure 4:
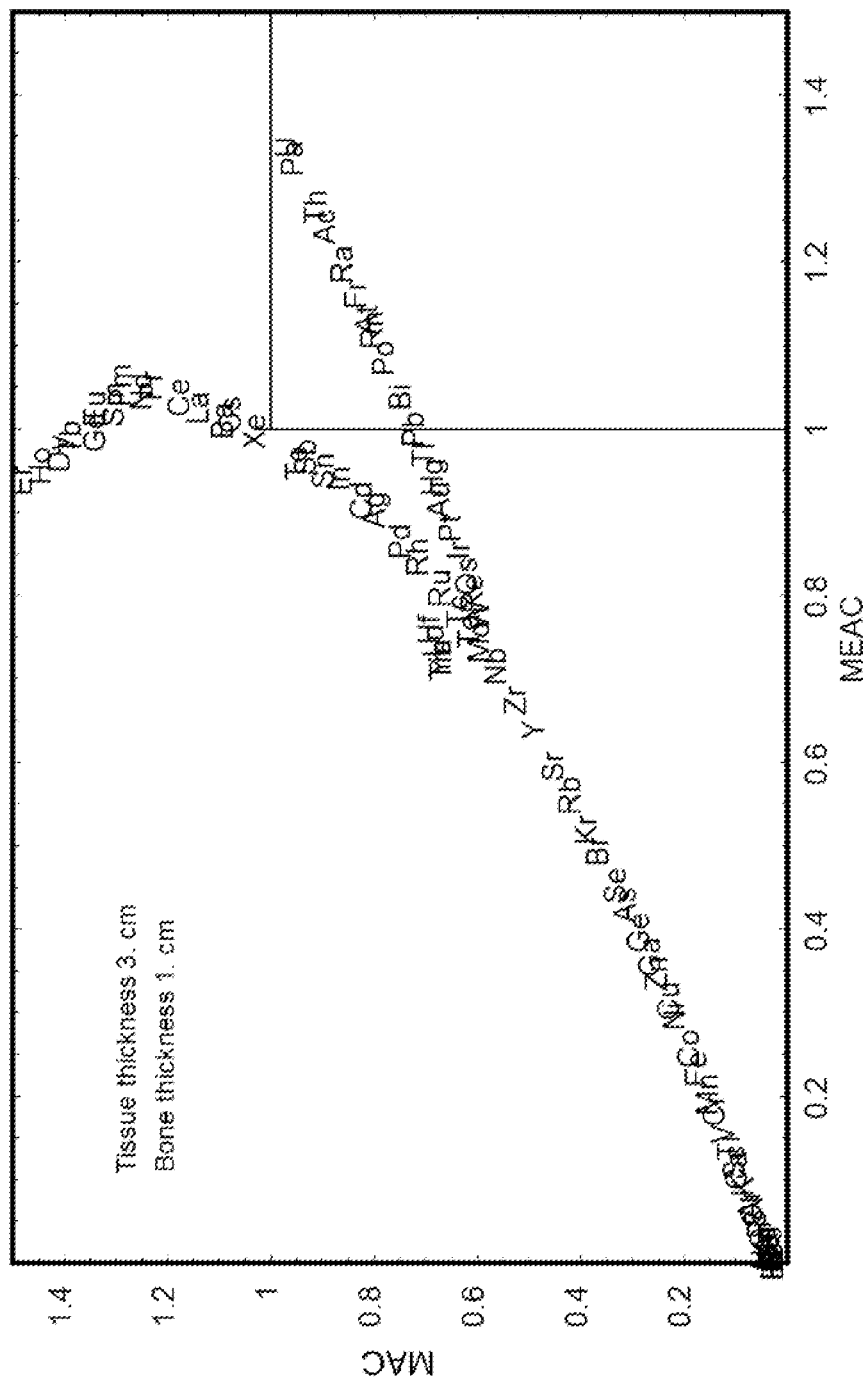
FIG. 4 depicts a 3 cm path of a 140 kVp X-ray beam through tissue overlayed with 1 cm of bone.

For example, the best high Z material compared to iodine can be different with bone (which hardens the radiation spectrum) between the radiation source and the target. In the FIGS. 3 and 4, the MAC is graphed against the MEAC for most elements in the periodic table. The box in the lower right hand corner delineates those elements which give the best potential enhancement of dosimetry relative to iodine for the particular target environment. FIG. 3 demonstrates that without bone in the 3 cm path of a 140 kVp X-ray beam, gold (Au) is an excellent choice for a contrast agent to enhance (MEAC) the radiation dose in a lesion by nearly 25% over iodine (I). At the same time, the beam would be attenuated 15% less than with iodine. However, in FIG. 4 with a 1 cm thickness of bone in the beam's path, gold (Au) has worse enhancement than iodine. In this case, bismuth (Bi) would be a better choice for the high Z element in the chelate. Bismuth gives a 5% dose enhancement compared to iodine but has 25% less attenuation in this setting. It is also noted for this example that the lanthanide series of elements would be less favorable choices.

This method of comparing the MAC to the MEAC of a high Z material relative to iodine (the latter is commonly used for conventional contrast agents) further increases the dose within a tumor or other diseased tissue, and reduces the amount of radiation received by the surrounding normal tissue.

The compounds and complexes of this invention can be provided as formulations in kit form so that the several of the components, for example, the ligand and the metal, are mixed at the appropriate time prior to use. Further, a pharmaceutically acceptable carrier may be required. Depending on solubility factors and the means of administration, and without intending to be limiting, such carriers can comprise, for example, water, aqueous alcohols, glycols, and phosphonate or carbonate esters, or other organic solvents. Physiologically acceptable suspending media, with or without adjuvants, can also comprise part of the formulation.

The following description is of the preferred mode of carrying out the invention. This description is made for the purpose of illustrating the general principles of the invention and should not be taken in a limiting sense.

All publications, patents and patent applications are herein incorporated by reference to the same extent as if each individual publication or patent application was specifically and individually indicated to be incorporated by reference.

The present invention is not to be limited in scope by the specific embodiments described herein, which are intended as single illustrations of individual aspects of the invention, and functionally equivalent methods and components are within the scope of the invention. Various modifications of the invention, in addition to those shown and described herein will become apparent to those skilled in the art from the foregoing description and accompanying drawings. Such modifications are intended to fall within the scope of the appended claims.

What is claimed is:

1. A method to combine high Z elements for delivery to a tumor in order to enhance the effect of ionizing x-ray radiation therapy, comprising:
   a. delivering an effective amount of a targeting agent to a diseased tissue wherein the targeting agent comprises a combination of heavy elements, each having an atomic number (Z) greater than 38 selected from the group consisting of La, Ce, Pr, Nd, Sm, Eu, Tb, Dy, Ho, Er, Tm, Yb, Lu and Ag, Sn, W, Re, Os, Ir, Au or Bi;
   b. wherein the targeting agent further comprises a ligand, a bone-targeting chelate, a soft tissue targeting chelate, a high payload targeting system, or a combination thereof to bind a high concentration of the heavy elements by functioning as an electron-pair donor in an electron-pair covalent bond formed with the heavy elements and selectively increasing the targeting agent in the diseased tissue;
   c. wherein neither the ligand, the bone-targeting chelate, the soft tissue targeting chelate nor the high payload targeting system is a biological carrier such as a protein, or a monoclonal antibody, or fragments thereof;
   d. wherein neither the heavy elements nor the targeting agent is radioactive-or becomes a radioactive isotope;
   e. administering external beam or brachytherapy ionizing x-ray radiation to interact with the greater cross-section of the heavy elements of the targeting agent in the diseased tissue;
   f. wherein the heavy element of the targeting agent enhances the diseased tissue's cross-section to ionizing x-ray radiation thereby creating additional ionizations and absorbed radiation dose.

2. The method according to claim 1 wherein the bone-targeting chelate is selected from the group consisting of ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), tris(2-aminoethyl) aminehexamethylenephosphonic acid (TTHMP), 1-carboxyethylenediaminetetramethylenephosphonic acid (CEDTMP) and bis(aminoethylpiperazine)tetramethylenephosphonic acid (AEPTMP), Ethylenediaminetetraacetic acid (EDTA), 1,4,7,10-tetraazacyclododecane-N,N',N'',N'''-tetramethylenephosphonic acid (DOTMP), hydroxyethyldiphosphonic acid (HEDP), methylenediphosphonic acid (MDP), diethylenetriaminepentaacetic acid (DTPA), hydroxyethylethylenediaminetriacetic acid (HEDTA), and nitrilotriacetic acid (NTA).

3. The method according to claim 1 wherein the targeting agent is used for the treatment of primary or metastatic bone cancer, or other primary or metastatic cancers.

4. The method according to claim 1 wherein the targeting agent is a soft tissue cancer-targeting agent comprising a tetraaza macrocyclic amine chelator with half ester phosphonic acid functionality capable of targeting soft tissue cancers.

5. The method according to claim 4 where the soft tissue cancer-targeting agent includes PCTMB or QCTME.

6. The method according to claim 1 wherein the targeting agent includes a high payload system consisting of a polymer comprising a fluorocarbon or a polyamine, or a particle comprising a nanoparticle or a liposome, capable of carrying a high payload comprising heavy elements and a targeting moiety.

7. The method according to claim 1 of using the targeting agent to both diagnose and treat pathological lesions in the head or body.

8. The method according to claim 1 of increasing the cross-section of a target to ionizing x-ray radiation relative to the cross-section of normal tissue wherein the increased cross-section results from the combination of heavy elements complexed with the chelate being deposited in the target comprising the steps of:
   a. determining the concentration of the targeting agent required to increase the target to non-target ratio of absorbed radiation dose by imaging with a CT scanner, or other imaging device; and, b. repeating the radiotherapy/treatment over a period of time.

\* \* \* \* \*